(12) United States Patent
Lai et al.

US006790318B2

(10) Patent No.: US 6,790,318 B2
(45) Date of Patent: Sep. 14, 2004

(54) METHOD OF PURIFICATION OF POLYMERIC MEDICAL DEVICE MATERIALS USING CONTINUOUS SOXHLET EXTRACTION

(75) Inventors: Yu-Chin Lai, Pittsford, NY (US); Dominic V. Ruscio, Webster, NY (US); David P. Vanderbilt, Webster, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 116 days.

(21) Appl. No.: 10/260,449

(22) Filed: Sep. 27, 2002

(65) Prior Publication Data

US 2004/0061829 A1 Apr. 1, 2004

(51) Int. Cl.[7] ................................................ B01D 11/00
(52) U.S. Cl. ....................... 202/169; 422/101; 623/6.56
(58) Field of Search ............................... 202/168–170, 202/175, 205–206, 235, 254; 528/480–503; 422/101, 280–281, 285, 288, 290; 604/289; 134/1, 10, 34, 37, 40; 203/81, 82, 84, 43; 159/22, 47.1, DIG. 16, 26; 623/6.11, 6.56

(56) References Cited

U.S. PATENT DOCUMENTS

| 3,937,680 | A | | 2/1976 | de Carle ............... 260/29.6 TA |
|---|---|---|---|---|
| D258,147 | S | | 2/1981 | Jennings et al. ............. D24/56 |
| 4,255,386 | A | * | 3/1981 | Schachter et al. .......... 422/101 |
| 4,265,860 | A | | 5/1981 | Jennings et al. ............ 422/280 |
| 4,664,666 | A | | 5/1987 | Barrett ......................... 623/6 |
| 5,258,490 | A | | 11/1993 | Chang ....................... 528/488 |
| 5,776,317 | A | | 7/1998 | Spring et al. ............... 202/168 |
| D413,678 | S | | 9/1999 | Anderson et al. .......... D24/232 |
| 6,660,208 | B2 | * | 12/2003 | Hanna ........................ 264/401 |

FOREIGN PATENT DOCUMENTS

EP  0 989 138 A2  3/2000

OTHER PUBLICATIONS

The Gregar Extractor, Online XP002268528 <URL:http://www.techtransfer.anl.gov/techtour/gregar.html> Jan. 23, 2004 pp.: three (3).

Technology Transfer at Argonne, Online XP002268529 <URL:http://chemistry.anl.gov/preview/Greg Jan. 23, 2004 pp.: three (3).

* cited by examiner

*Primary Examiner*—David J. Isabella
*Assistant Examiner*—Urmi Chattopadhyay
(74) *Attorney, Agent, or Firm*—Rita D. Vacca

(57) ABSTRACT

A process for removing contaminants and/or leachables from polymeric materials useful in the manufacture of biocompatible medical devices such as intraocular lenses, corneal inlays and contact lenses using continuous soxhlet extraction.

10 Claims, 2 Drawing Sheets

METHOD OF PURIFICATION OF POLYMERIC MEDICAL DEVICE MATERIALS USING CONTINUOUS SOXHLET EXTRACTION

FIELD OF THE INVENTION

The present invention relates to a method of polymer purification through continuous soxhlet extraction useful in the manufacture of biocompatible polymeric medical devices. More particularly, the present invention relates to a method of removing contaminants and/or leachables from polymeric materials useful in the manufacture of biocompatible medical devices such as intraocular lenses, corneal inlays and contact lenses using continuous soxhlet extraction.

BACKGROUND OF THE INVENTION

Medical devices are designed for particular medical applications. Many medical devices are manufactured from polymeric materials, which must be free from contaminants and/or leachables to be useful for the particular medical application for which it is designed. If not removed, contaminants and/or leachables in the material of medical devices may cause adverse effects on patient health or the ultimate outcome of the medical procedure. Such adverse effects can be so severe as to defeat the original purpose of conducting the medical procedure.

In the case of medical devices for ocular use such as but not limited to contact lenses, corneal inlays and intraocular lenses, the devices must be relatively free from contaminants and/or leachables. In medical device applications, contaminants and/or leachables usually form in the polymeric materials of the medical devices as a side product from incomplete curing of the material monomers and/or prepolymers. Material contaminants and/or leachables may likewise be preexisting impurities present in the material monomers and/or prepolymers prior to curing. Because such material contaminants and/or leachables are not uncommon, thorough material extraction is a required step in the manufacture of medical devices and particularly medical devices for ocular use.

There are many ways to extract polymeric medical device materials to remove contaminants and/or leachables present therein. The most commonly used method is batch extraction. Batch extraction is accomplished by placing polymeric medical devices in a container filled with a quantitative amount of "clean" solvent. The clean solvent selected must be capable of swelling the material of the medical device substantially such that contaminants and/or leachables in the material are free to leave the medical device material and enter the solvent phase. The swelled and purified polymeric medical device is then removed from the "dirty" solvent.

Batch extraction of polymeric medical device materials as just described works well in most cases. However, batch extraction may not be sufficiently effective in cases where the target application of the medical device has very stringent requirements in terms of low levels of impurities and/or leachables. Additionally, batch extraction is cumbersome in that it requires the use of large quantities of clean solvent and requires frequent solvent replacement. Frequent solvent replacement causes extraction disruption and increased costs. Batch extraction is likewise not evironmentally friendly in that the process creates large quantities of dirty waste solvent.

Another type of batch extraction is a soxhlet extraction. In a soxhlet extraction, clean solvent contained in a flask is heated to a boil. The solvent vapor evaporates through a vapor arm of a condenser and then condenses within a chamber of the condenser by the running of cold water through a portion of the condenser. The condensed solvent, while still hot, drops down into a reservoir containing the devices to be extracted or purified. The polymeric device materials thus swell and the contaminants and/or leachables are free to leave the device via the solvent. Once the liquid level in the reservoir is above the top level at the peak of the liquid arm, nearly all solvent in the resevoir flows out through the liquid arm and is recycled back to the flask along with the material contaminants and/or leachables. The reservoir is then gradually refilled with condensed hot solvent and the extraction process repeats again, i.e., the devices are again submerged in the rising solvent level until the solvent gets recycled. The soxhlet extraction process as just described is a batch extraction, although slightly better than conventional batch extractions since the solvent is recycled.

Because of the noted shortcomings of batch extraction of polymeric medical device materials, there is a need for an improved method of extracting contaminants and/or leachables from polymeric materials.

SUMMARY OF THE INVENTION

Polymeric medical device materials such as those useful in the manufacture of contact lenses, corneal inlays and intraocular lenses are produced with sufficiently low levels of contaminants and/or leachables in accordance with the present invention through a novel continuous soxhlet extraction process. The continuous soxhlet extraction process of the present invention eliminates difficulties formerly encountered in the purification of polymeric medical device materials using batch extraction. The subject continuous soxhlet extraction process is effective in achieving sufficiently low levels of contaminants and/or leachables in cases where the target application of the medical device has very stringent requirements in terms of low levels of impurities and/or leachables. Additionally, the continuous soxhlet extraction process of the present invention is relatively simplistic in that it does not require the use of large quantities of solvent and does not require frequent solvent replacement. Because there is no need for frequent solvent replacement, extraction disruptions and solvent costs are reduced. Additionally, continuous soxhlet extraction in accordance with the present invention is an environmentally friendly purification process since large quantities of dirty waste solvent are not produced.

Accordingly, it is an object of the present invention to provide an effective purification process for polymeric medical device materials.

Another object of the present invention is to provide an effective purification process for polymeric medical device materials with target applications having very stringent requirements in terms of low levels of impurities and/or leachables.

Another object of the present invention is to provide an effective purification process for polymeric medical device materials that reduces clean solvent requirements.

Another object of the present invention is to provide an effective purification process for polymeric medical device materials that reduces solvent waste production.

Still another object of the present invention is to provide an effective purification process for polymeric medical device materials that is economical and environmentally friendly.

These and other objectives and advantages of the present invention, some of which are specifically described and others that are not, will become apparent from the detailed description, drawings and claims that follow.

DETAILED DESCRIPTION OF THE INVENTION

Figure 1:
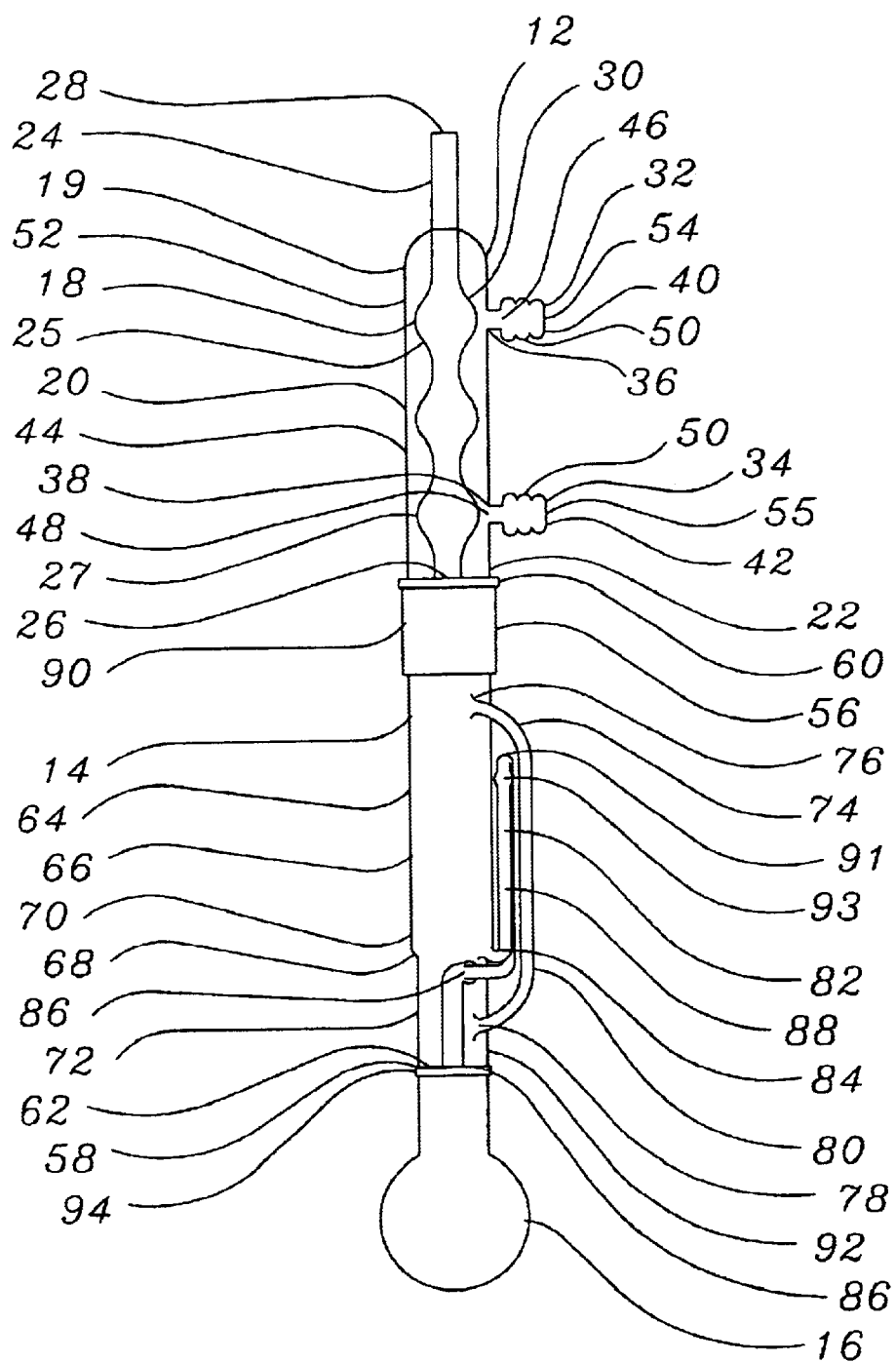
FIG. 1 is a side view of an extraction unit with a soxhlet extractor.

The present invention relates to a novel continuous soxhlet extraction process for the extraction of contaminants and/or leachables from polymeric medical device materials. Typically, an assembled soxhlet extraction unit 10, as illustrated in FIG. 1, consists of three typically glass-fabricated components, i.e., a condenser 12, a soxhlet extractor 14 and a flask 16. Condenser 12 is generally an elongated tubular device. Condenser 12 includes an inner portion 18 partially encapsulated by a generally tubular outer housing 20. Inner portion 18 is elongated with opposed attachment end 22 and free end 24. Between opening 26 of attachment end 22 and opening 28 of free end 24 is chamber 30 defined by interior surface 25 of inner portion 18. Extending a distance beyond exterior surface 27 of inner portion 18 between free end 24 and attachment end 22 so as to encapulate the same is outer housing 20. Outer housing 20 is equipped with an inlet port 32 and an outlet port 34. Inlet port 32 and outlet port 34 are each generally tubular with attached ends 36 and 38 respectively, and free ends 40 and 42 respectively. Attached ends 36 and 38 are attached to or unitarily formed on exterior surface 44 of outer housing 20. Exterior surface 50 of free ends 40 and 42 may be completely or partially textured to allow secure attachment of friction fitted tubing. Free ends 40 and 42 each have openings 54 and 55 in fluid communication with interior channels 46 and 48 of inlet port 32 and outlet port 34 respectively. Interior channels 46 and 48 are likewise in fluid communication with chamber 19 between interior surface 52 of outer housing 20 and exterior surface 27 of inner portion 18.

Soxhlet extractor 14 is where the extraction or purification of the polymeric medical device material occurs and has an unique design. Extractor 14 is an elongated generally tubular device. Extractor 14 has opposed enlarged end 56 and attachment end 58. Enlarged end 56 and attachment end 58 each have openings 60 and 62 respectively, in fluid communication with chamber 64. Chamber 64 is defined by interior surface 66 of extractor 14. Extending from enlarged end 56 until reduction point 68, extractor 14 includes a body portion 70 of a particular diameter. Extending from reduction point 68 to attachment end 58 is tail portion 72 having a particular diameter less than that of body portion 70. Body portion 70 of extractor 14 serves as a reservoir to directly hold the polymeric medical devices to be extracted, or alternatively, to directly hold a glass or cellulosic thimble in which the polymeric medical devices are placed. A side vapor arm 74 has two opposed attached ends 76 and 78 with an open passage 80 therebetween. One attached end 76 connects to body portion 70 near enlarged end 56 and the other attached end 78 connects to body portion 70 near attachment end 58. Open passage 80 of vapor arm 74 is in fluid communication with chamber 64. A side liquid arm 82, which serves as a siphoning tube, has opposed attachment end 84 and free end 86 with an open passage 88 therebetween. Attached end 84 connects to body portion 70 adjacent reduction point 68 and extends upward toward enlarged end 56 parallel exterior surface 90 of body portion 70 to a point just below attached end 76 and then loops 180 degrees to form peak 91 and extends back toward attachment end 58. Near attachment end 58 liquid arm 82 passes through wall 92 of extactor 14 into chamber 64 to terminate as free end 86 within attachment end 58. For purposes of the present invention, the diameter of liquid arm 82 is reduced by at least approximately twenty to thirty percent from that of standard sized soxhlet extractors. Optionally, liquid arm 82 may have a relatively small chamber 93 of slightly enlarged diameter than that of passage 88 located between attached end 84 and peak 91.

Alternatively, a Gregar™ extractor (Kontes, Inc., Vineland, N.J.) 100, illustrated in FIG. 2, may be used in place of soxhlet extractor 14 for purposes of the present invention as described in more detail below. Gregar extractor 100 is a generally elongated device. Gregar extractor 100 has opposed enlarged end 102 and attachment end 104. Enlarged end 102 and attachment end 104 each have openings 106 and 108 respectively, in fluid communication with chamber 110. Chamber 110 is defined by interior surface 112 of extractor 100. Extending from enlarged end 102 until reduction point 114, extractor 100 includes a body portion 116 of a particular diameter. Extending from reduction point 114 to attachment end 104 is tail portion 118 having a particular diameter less than that of body portion 116. Body portion 116 of extractor 100 serves as a reservoir to directly hold polymeric medical devices to be extracted, or alternatively, to directly hold a glass or cellulosic thimble in which polymeric medical devices are placed. A side vapor arm 120 has two opposed attached ends 122 and 124 with an open passage 126 therebetween. One attached end 122 connects to body portion 116 near enlarged end 102 and the other attached end 124 connects to body portion 116 at tail portion 118 near attachment end 104. Open passage 126 of vapor arm 120 is in fluid communication with chamber 110. A side liquid arm 128, which serves as a siphoning tube, has opposed attachment ends 130 and 132 with an open passage 134 therebetween. Attachment end 130 connects to body portion 116 just below attached end 122. Attachment end 132 connects to tail portion 118 just above attachment end 124. Gregar extractor 100 likewise is equipped with two adjustable valves 136 and 138. Adjustable valve 136 is positioned in liquid arm 128 near attachment end 130. At adjustable valve 136 is connection portion 140 defining passage 142 in fluid communication with open passage 134 through adjustable valve 136 and with open passage 126. Adjustable valve 138 is positioned in tail portion 118 at attachment end 132.

Flask 16 is preferably a standard 500 mL round bottom flask with a neck opening 94 sized to accept attachment end 58 of extractor 14 or attachment end 104 of extractor 100. Likewise, opening 60 of enlarged end 56 of extractor 14 or opening 106 of enlarged end 102 of extractor 100 is sized to accept attachment end 22 of condenser 12.

Figure 2:
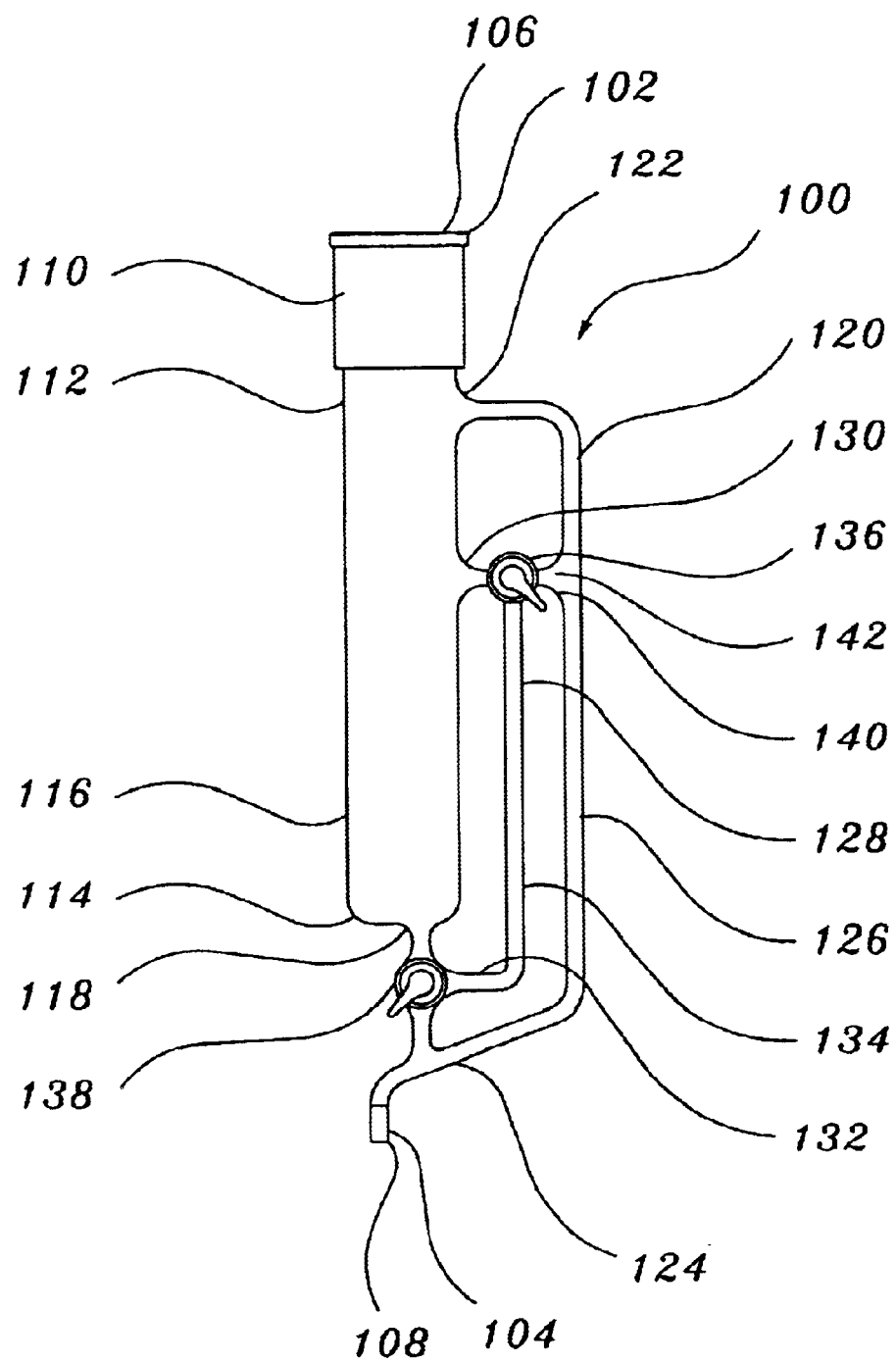
FIG. 2 is a side view of a gregar extractor.

Continuous soxhlet extraction using for example the assembled soxhlet extraction unit 10 of FIG. 1 or an extraction unit utilizing gregar extractor 100 of FIG. 2 offers better efficiency in extraction as compared to batch extraction. To perform the continuous soxhlet extraction process of the present invention using soxhlet extractor 14, polymeric medical devices to be extracted or purified are placed inside a glass or cellulosic thimble with or without a coarse sintered glass filter or like filter base therein to increase solvent flow. A suitable solvent, approximately 180 cc, is placed in flask 16. Suitable solvents for purposes of the present invention include good solvents for the ingredients used in fabricating the medical devices to be purified/cleaned. Such solvents include for example but are not limited to isopropanol, ethanol, water, tetrahydrofuran and toluene. Heat is then applied to the flask to bring the solvent to a boil. At this time, tubing is attached to inlet port 32 and outlet port 34 of condenser 12 for the circulation of cooling fluid, preferably water, within chamber 19. The circulation of a cooling fluid within chamber 19 aids in the condensation of solvent vapor within condenser 12. Condensed solvent then runs down from condenser 12 to extractor 14 and in contact with the polymeric medical device material to be purified. A liquid arm 82, modified to be approximately twenty to thirty percent smaller in diameter than that of standard sized soxhlet extractors, is used in the present process such that a greater imbalance in pressure is required for solvent to recycle back to flask 16. Alternatively, an extractor with three-way joints and dual adjustable valves to allow solvent flow through vapor arm 74, similar to that of Gregar™ extractor 100 of FIG. 2 can be used. By so altering the configuration of the soxhlet extractor 14, or by substituting soxhlet extractor 14 with Gregar extractor 100, continuous flow of solvent is achieved throughout the extraction process. The polymeric medical device materials to be extracted or purified are thereby continuously submerged within a flow of clean solvent. Accordingly, the subject continuous soxhlet extraction is more efficient and does not disrupt the medical device extraction or purification process with material swelling and deswelling phases as is the case during batch extraction processes. Other advantages of the subject continuous soxhlet extraction include the ability to use a higher extraction temperature and the ability to freely adjust extraction temperature depending on process needs. These advantages with regard to extraction temperature allow for a more efficient extraction process. Additionally, the subject continuous soxhlet extraction process allows for rapid solvent recovery and thus sharply reduces the amount of solvent required for the extraction process. Reduced solvent requirements are both economically and environmentally favorable.

Examples of polymeric materials useful in the manufacture of medical devices, which may be purified or extracted to remove various contaminants and/or leachables in accordance with the present invention include but are not intended to be limited to hydrophobic acrylics, hydrophilic acrylics, silicone-based polymers and the like.

The method of purification of polymeric medical devices using continuous soxhlet extraction in accordance with the present invention is described in still greater detail in the examples that follow. In each example, silicone intraocular lenses as cured and released from molds were used for the extraction studies. All lenses were of the same model, i.e., Model LI61U, (Bausch & Lomb, Incorporated, Rochester, N.Y.) and cast at the same time, i.e., of the same lot.

EXAMPLE 1

Static Solvent Extraction at Ambient Temperature

Ten (10) intraocular lenses with a dry weight of 0.3231 g, were submerged and settled on the bottom of a flask filled with 180 cc of isopropanol (IPA). After 3 hours, all lenses were recovered and dried in vacuum oven at 70° C. overnight. The weight of the dried lenses was 0.3144 g, for a loss of 2.69 percent.

EXAMPLE 2

Batch Soxhlet Extraction with Lens Samples in Teflon™ Holder

A soxhlet extractor capable of holding 180 cc of solvent without overflow was attached to a 500 mL round bottom flask filled with IPA and a refluxed condenser. The variance was adjusted and the IPA was heated to reflux. The temperature of the main body of the soxhlet extractor was found to be 75° C.

Ten (10) intraocular lenses with a dry weight of 0.3223 g were placed in open cages cut out from circular Teflon™ (E.I. Dupont de Nemours, Wilmington, Del.) plates (5 cages on each plate). The Teflon™ plates were then stacked vertically and held together using a central holder. The holder with the plates and lenses was then placed in the soxhlet extractor and underwent extraction for three hours. During the extraction, all solvent siphoned back into the flask once the level of the solvent within the extractor reached a level above that of the peak of the liquid arm. After three hours of extraction, the lenses were removed from the Teflon™ plates. The lenses were then dried under vacuum at 70° C. overnight. The weight of the dried lenses was 0.3112 g, for a loss of 3.44 percent.

EXAMPLE 3

Batch Soxhlet Extraction with Lens Samples in Glass Thimble with Coarse Sintered Glass Filter Ten (10) intraocular lenses having a dry weight of 0.3216 g were placed in a glass thimble on top of a coarse sintered glass filter placed in the bottom thereof. The glass thimble was then placed in a soxhlet extractor attached to a flask and a condenser. The lenses then underwent extraction for three hours. During the extraction, all solvent except for the solvent within the glass thimble was recycled once the level of the solvent within the extractor reached a level above that of the peak of the liquid arm. Accordingly, the lenses were continuously submerged in solvent throughout the extraction process although solvent flow was not continuous due to recycling. After extraction, the lenses were removed from the glass thimble and air dried for three hours. The lenses were then dried under vacuum at 70° C. overnight. The weight of the dried lenses was 0.3105 g, for a loss of 3.45 percent.

EXAMPLE 4

Continuous Soxhlet Extraction with Lens Samples in Glass Thimble with Coarse Sintered Glass Filter Ten (10) intraocular lenses weighing 0.3221 g were extracted using the same process as that described in Example 3 except a soxhlet extractor with a twenty to thirty percent smaller diameter liquid arm than that of a standard sized extractor was used. The smaller diameter liquid arm allowed for continuous flow of used solvent through the liquid arm. After extraction, the lenses were removed from the glass thimble and air dried for three hours. The lenses were then dried under vacuum at 70° C. overnight. The weight of the dried lenses was 0.3091 g for a loss of 4.04 percent.

EXAMPLE 5

Extended Continuous Soxhlet Extraction

To determine the total possible level of extractable of lenses of interest, the dried lenses from Example 4 were placed back into the extraction setup as described in Example 4 and extracted for an additional twenty-four hours. After extraction, the lenses were removed from the glass thimble and air dried for three hours. The lenses were then dried under vacuum at 70° C. overnight. The weight of the dried lenses was 0.3090 g, indicating that the initial 3 hours of continuous soxhlet extraction of Example 4 was enough to remove nearly all extractables.

A comparison of the percentage of extractables from Examples 1 through 4 indicates that continuous soxhlet extraction is more efficient than static extraction at ambient temperature and batch soxhlet extraction processes.

In addition to contact lenses, corneal inlays and intraocular lenses, the subject continuous soxhlet extraction process of the present invention is also suitable for use in the production of other polymeric medical devices such as but not limited to keratoprostheses, capsular bag extension rings, corneal rings and like devices.

Polymeric medical devices purified or extracted using the process of the present invention are used as medically customary. For example, in the case of a contact lens purified or extracted in accordance with the present invention, the contact lens is simply positioned on the cornea of an eye as customary. Another example, in a surgical cataract procedure, an incision is placed in the cornea of an eye. Through the corneal incision the cataractous natural lens of the eye is removed (aphakic application) and an intraocular lens purified or extracted in accordance with the process of the present invention is inserted into the anterior chamber, posterior chamber or lens capsule of the eye prior to closing the incision. Still another example, an incision is placed in an eye and an intraocular lens purified or extracted in accordance with the process of the present invention is inserted in the anterior chamber or posterior chamber of the eye without removal of the natural lens (phakic application) prior to closing the incision. As described the subject ophthalmic devices may be used as customary in a variety of medical procedures known to those skilled in the field of ophthalmology.

While there is shown and described herein a process for continuous soxhlet extraction of polymeric materials from which medical devices are comprised, it will be manifest to those skilled in the art that various modifications may be made without departing from the spirit and scope of the underlying inventive concept and that the same is not limited to particular processes and structures herein shown and described except insofar as indicated by the scope of the appended claims.

We claim:

1. A method of continuous soxhlet extraction for the purification of polymeric materials comprising:
   assembling a flask, an extractor with a liquid arm dimensioned to enable continuous solvent flow and a condenser;
   placing polymeric materials in said extractor and solvent in said flask; and
   heating said solvent to create a flow of said solvent through said condenser, extractor and flask for purification of said polymeric materials.

2. The method of claim 1 wherein said condenser is cooled by the flow of a contained fluid.

3. The method of claim 1 wherein said condenser is cooled by the flow of contained water.

4. The method of claim 1 wherein said extractor is a soxhlet extractor.

5. The method of claim 1 wherein said polymeric materials are in the form of medical devices.

6. The method of claim 1 wherein said polymeric materials are in the form of medical devices selected from the group consisting of contact lenses, corneal inlays, corneal rings, intraocular lenses, keratoprostheses and capsular bag extension rings.

7. The method of claim 1 wherein said polymeric materials are selected from the group consisting of hydrophobic acrylics, hydrophilic acrylics and silicone-based polymers.

8. The method of claim 1 wherein said polymeric materials are placed within a glass or cellulose thimble within said extractor.

9. The method of claim 1 wherein said polymeric materials are placed within a glass or cellulose thimble with a sintered glass filter in the bottom of said thimble.

10. The method of claim 1 wherein said solvent is selected from the group consisting of isopropanol, ethanol, water, tetrahydrofuran and toluene.

* * * * *